United States Patent [19]
Yapp

[11] Patent Number: 5,548,985
[45] Date of Patent: Aug. 27, 1996

[54] ROD BENDER FOR FORMING SURGICAL IMPLANTS IN THE OPERATING ROOM

[76] Inventor: Ronald A. Yapp, 3330 E. Colter St., Phoenix, Ariz. 85018

[21] Appl. No.: 242,169

[22] Filed: May 13, 1994

[51] Int. Cl.⁶ .................... B21D 7/04; B21D 9/05
[52] U.S. Cl. .................... 72/149; 72/157; 72/479
[58] Field of Search ............. 72/149, 157, 450, 72/479

[56] References Cited

U.S. PATENT DOCUMENTS

| 4,926,672 | 5/1990 | Swanson | 72/458 |
| 5,148,695 | 9/1992 | Ellis | 72/149 |

FOREIGN PATENT DOCUMENTS

| 1132047 | 3/1957 | France | 72/149 |
| 2206069 | 12/1988 | United Kingdom | 72/149 |

*Primary Examiner*—David Jones
*Attorney, Agent, or Firm*—Michael A. Lechter

[57] ABSTRACT

A bender for bending metal rod to form surgical implants in a sterile operating room environment. The bender being made of an autoclavable material having a hardness greater than the maximum hardness of the rod to be bent. The bender includes a capstan, a primary mandrel, a gripping element, and a follower mandrel. The primary mandrel, which rotates with the capstan, includes at least one generally cylindrical portion with a guide channel formed in the periphery thereof. The follower mandrel also includes at least one generally cylindrical portion with a guide channel formed in the periphery thereof. The follower guide channels are disposed in planar alignment with the corresponding guide channel of the primary mandrel to form bending channels therebetween. The gripping member is mounted for rotation with said primary mandrel, and encloses a portion of the primary mandrel guide channel(s) to form a passageway of predetermined configuration. The passageway(s) is configured such that when the primary mandrel is rotated to a predetermined position, said passageway is brought into general alignment with the corresponding bending channel, and the rod can be journaled through the passageway and through the bending channel without bending.

19 Claims, 3 Drawing Sheets

ROD BENDER FOR FORMING SURGICAL IMPLANTS IN THE OPERATING ROOM

FIELD OF THE INVENTION

The present invention relates to surgical devices, and particularly to a device for bending metal rod in the environment of the operating room to form surgical implants.

BACKGROUND OF THE INVENTION

Surgeons often use metal rods of predetermined diameter, e.g. in the range of 3/16ths to 5/16ths inch, in splinting portions of the human skeleton, e.g. to effect fusing of adjacent vertebrae in the spine. The skeleton, however, is multi-curved, and the rod must be bent to conform to the curvature of the bone in order to maximize affixation between the splinted portions of the skeleton. For example, in many instances, a surgically implanted splint includes respective parallel legs, preferably disposed in a common plane, and an arcuate bridge connecting the legs, disposed in a plane transverse to that of the legs. When implanted, the legs of the splint extend along opposing sides of the respective portions of the skeleton, and with the arch angled towards the exterior, bridging the skeleton, to maintain the legs in position to fix the relative disposition of the skeletal portions.

An example of such an implant is shown in FIGS. 1A and 1B. Specifically, a splint implant 100 is disposed to fix the relative disposition of respective vertebrae C1 and C2 at the base of a patient's occiput 102. Implant 100 includes respective parallel legs 106 and 108, connected by a generally U-shaped bridge 110. As best seen in FIG. 1A, respective legs 106 and 108 are disposed in parallel, extending along opposing sides of vertebrae C1 and C2 for a predetermined distance above and below the vertebrae. As best seen in FIG. 1B, bridge 110 is bent at an angle transverse to the plane of legs 106 and 108, coupling legs 106, while accommodating the patient's anatomical structure.

Historically, pre-bent splinting implants have been employed by surgeons. However, commercially available pre-bent implants are provided in specific sizes (e.g. small; medium; and large). Because the splinting implants do not typically meet morphological fit requirements, surgeons have generally reconfigured the bone to fit the implant. This process typically involves removing, e.g. grinding or cutting away, portions of the bone, and tends to be both time consuming and traumatic to the patient. Further, while the general configuration of a splinting implant for particular portions of the skeleton can be determined by x-ray and imaging techniques, in many instances it is desirable to confirm the desired configuration of the implant by visual inspection of the skeletal portions at issue. Accordingly, it is desirable that the surgeon be able to shape bendable metallic rods to form custom implants during surgery to meet the specific anatomical fit requirements of a patient.

Attempts have been made to form implants in the operating room during surgery by bending rods into the desired configuration. However, bending was effected employing pliers, vices, and hammers. While rod benders are, in general, known, the devices typically can bend the rod only to a single particular radius and are not shielded to protect against debris flying in the event that a rod breaks, but nonetheless tend to be relatively complex devices, including closed holes, cervices, and interstices, in which blood or tissue is often retained, and are difficult to disassemble for cleaning. Such devices are thus difficult to clean and sterilize e.g. by autoclaving, for use in the operating room.

Significantly, the prior techniques for custom bending of rod to form implants in the operating room, have tended to nick, scratch, gouge, or kink the surgical implant. Such marring tends to form stress risers, and to lead to early fatigue failure of the implant. Specifically, in situ, the splint implant is subject to relatively high stresses. While healthy bone typically replaces itself, thus accommodating wear from such stresses, that is not the case with a metal implant; normal stresses tend to fatigue the metal of the implant. Marring, such as any nicks, scratches, gouges, or the like in the implant, tends to produce very high stresses at the root of the mar, tending to make the implant more susceptible to bending and ultimate failure.

Fabrication of the implant in the operating room has also tended to involve a significant period of time, e.g. 20 to 25 minutes.

Accordingly, there is a need for an apparatus for custom forming of implants from metal rod in the operating room, quickly and economically, without marring the surface of the rod, and which is simple and readily disassemblable, and autoclavable to ensure proper sterilization.

SUMMARY OF THE INVENTION

The present invention provides a particularly advantageous apparatus for bending metal rod to form surgical implants in a sterile operating room environment, with minimal nicking and scratching of, and minimal transfer of foreign material to the rod. In accordance with one aspect of the invention, the bender includes a capstan, a primary mandrel, a gripping element, and a follower mandrel. The primary mandrel, which rotates with the capstan, includes at least one generally cylindrical portion with a guide channel formed in the periphery thereof.

The follower mandrel also includes at least one generally cylindrical portion with a guide channel formed in the periphery thereof. The follower guide channels are disposed in planar alignment with the corresponding guide channel of the primary mandrel to form bending channels therebetween.

The gripping member is mounted for rotation with said primary mandrel, and encloses a portion of the primary mandrel guide channel(s) to form a passageway(s) of predetermined configuration. The passageway(s) is configured such that when the primary mandrel is rotated to a predetermined position, said passageway is brought into general alignment with the corresponding bending channel, and the rod can be journaled through the passageway and through the bending channel without bending.

The capstan, primary mandrel, gripping member, and follower mandrel are formed of an autoclavable material with a predetermined hardness greater than the maximum hardness of the rod to be bent.

BRIEF DESCRIPTION OF THE DRAWING

A preferred exemplary embodiment of the present invention will hereinafter be described in conjunction with the appended drawing, wherein like designations denote like elements, and.

DETAILED DESCRIPTION OF A PREFERRED EMBODIMENT

Figure 1A:
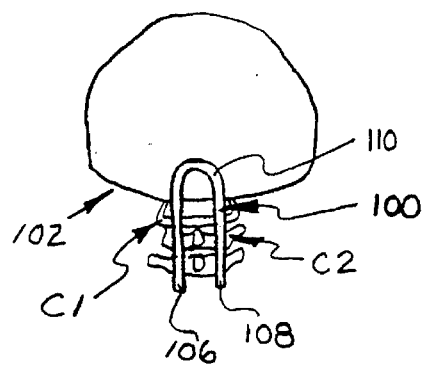
FIG. 1A and B are schematic illustrations of an implant of the type formed by apparatus in accordance to present invention.
Figure 1B:
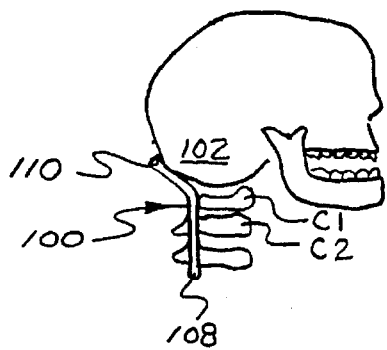
Figure 2:
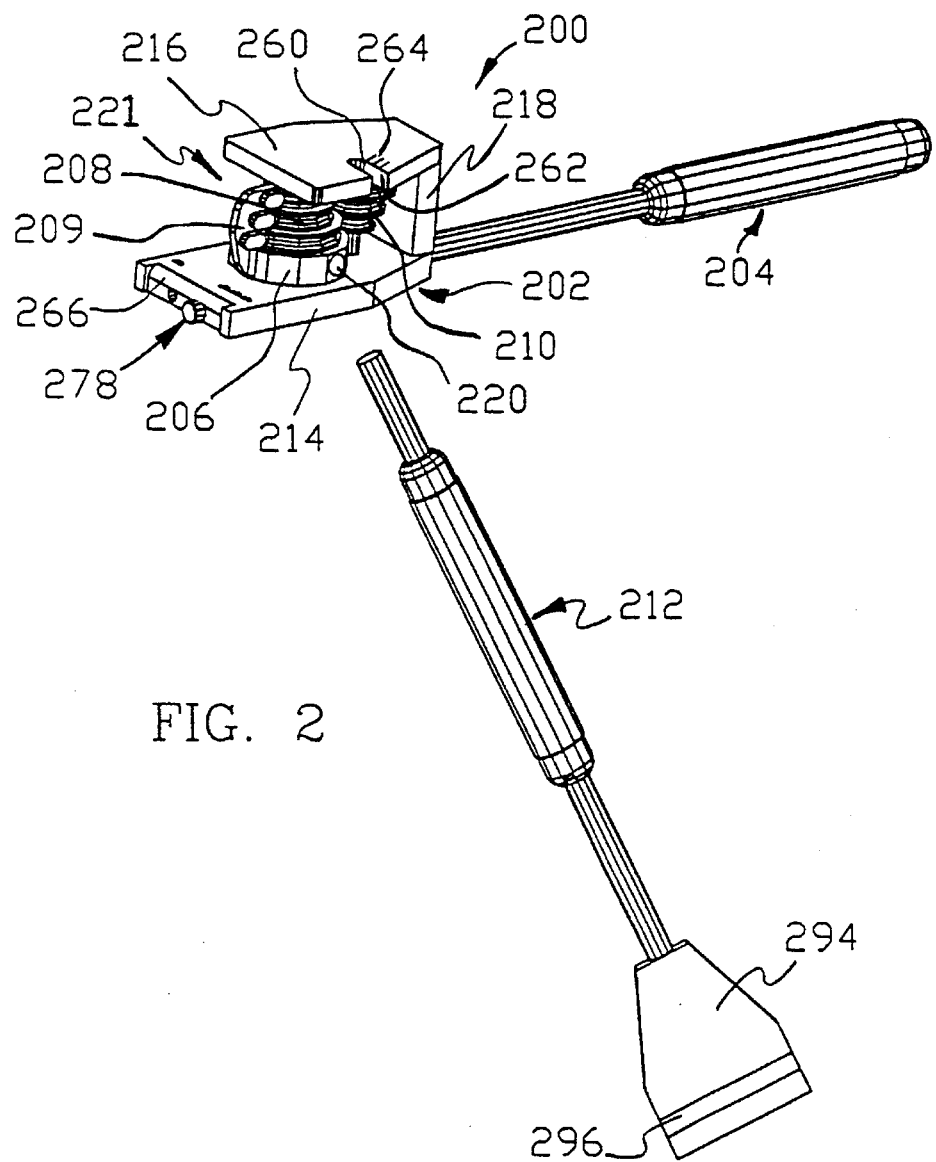
FIG. 2 is a pictorial illustration of a surgical rod bending device in accordance with the present invention.

Referring now to FIG. 2, a surgical rod bender 200, in accordance with the present invention, comprises: a mandrel housing 202; a first lever arm, e.g. handle 204; a capstan 206; a primary mandrel 208; a rod gripping element, e.g. rod grip plate, 209; a follower mandrel 210; and a second, preferably removable, lever arm 212.

Mandrel housing 202 suitably comprises a base plate 214, a top plate 216, and an end plate (back) 218. Base plate 214 is suitably removably fastened to end plate 218. Top plate 216 is likewise removably connected to end plate 218. If desired, one of base plate 214 or top plate 216 can be formed integrally with end plate 218. Base plate 214 and top plate 216 are disposed generally in parallel planes, offset from each other by a predetermined distance, forming, together with end plate 218, a chamber, generally indicated as 221, open on three sides in the direction of the distal end of housing 202.

Lever arm 204 suitably extends rearwardly preferably perpendicularly, from end plate 218, in a plane a predetermined distance above the upper (interior) surface of base plate 214. As will hereinafter be discussed, first lever arm 204 and second lever arm 212 when received by capstan 206 are disposed in a common plane. If desired, lever arm 204 can be formed integrally with end plate 218.

Housing 202 and lever arms 204 and 212 are all formed of rugged, autoclavable materials, not subject to oxidation when subjected to water or steam, e.g. 304 stainless steel. If desired, handle grips formed of an autoclavable plastic such as polyacetal (e.g. Delrin) may be disposed on lever arms 204 and 212.

Figure 3:
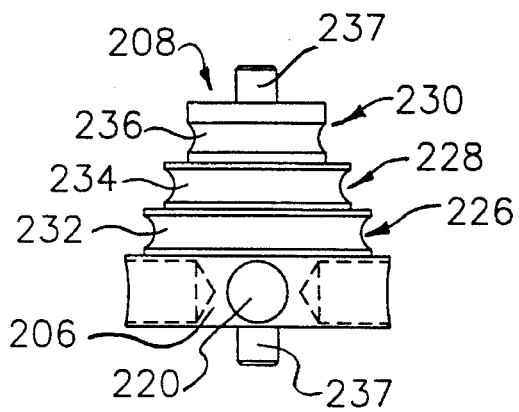
FIG. 3 is a side view of the primary mandrel of the apparatus of FIG. 2.

Capstan 206 is disposed between plates 214 and 216, disposed for rotation about a predetermined axis. Capstan 206 is employed to radially receive second lever arm 212, and impart rotation to primary mandrel 208. Referring now to FIGS. 2 and 3, capstan 206 suitably comprises a cylinder of predetermined radius and height, including a plurality, e.g. four, of radially disposed bores 220 of a predetermined diameter, e.g. ⅜ths inch. The height of capstan 206 is sufficiently in excess of the bore diameter to avoid any thin edges that might chip or break. In operation, bores 220 receive the end of second lever arm 212 to provide a mechanical advantage in effecting rotation of primary mandrel 208. Bores 220 are disposed in the same plane as first lever arm 204, to ensure lever arms 204 and 212 can be moved toward each other during the bending process without generating any spurious torques.

Primary mandrel 208 is employed as the element about which the rod is bent, and controls the configuration of the bend. Primary mandrel 208 is disposed between plates 214 and 216, preferably in axial alignment with capstan 206 and rotates with capstan 206. Primary mandrel 208 suitably comprises a predetermined number, e.g. three, of stacked cylinders 226, 228 and 230, of decreasing diameter. A respective guide channel 232, 234 and 236 is formed in the peripheral sidewalls of cylinders 226, 228 and 230. The configurations of guide channels 232, 234 and 236 are chosen in accordance with the maximum diameter of the rods to be bent. The diameter of the respective cylinders, measured at the interior of guide channels 232, 234 and 236, correspond to respective diameters of curvatures to which the rod is to be bent. Suitable diameters of curvature for forming splinting implants for the human spine are 1¼ inch, 1 inch, and ¾ of an inch. As will hereinafter be more fully discussed, bender 200 can accommodate a variety of interchangeable primary mandrels having different diameters, and combinations of diameters.

Respective axial pins 237 extending perpendicularly from plates 214 and 216, e.g. rotatably engaged in respect bores in plates 214 and 216, provide an axes of rotation for capstan 206 and primary mandrel 208. In the preferred embodiment, capstan 206, primary mandrel 208 and axial pins 237 rotatably engaged in respect bores in plates 214 and 216, are formed as an integral unit to simplify disassembly and reassembly, and sterilization.

Figure 4:
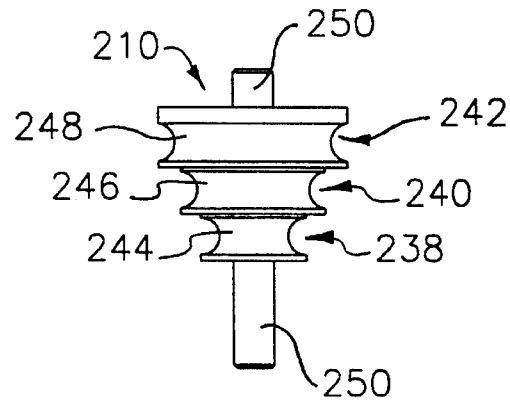
FIG. 4 is a side view of the follower mandrel of the apparatus of FIG. 2.

Follower mandrel 210 is employed to roll against the rod during the bending process, causing the rod to conform to the guide channel of primary mandrel 208. Referring now to FIGS. 2 and 4, follower mandrel 210 comprises a predetermined number, e.g. three, of stacked cylinders 238, 240 and 242 of increasing diameter. Each of the cylinders includes a respective peripheral guide channel 244, 246 and 248. The heights of cylinders 238, 240 and 242 correspond to the heights of primary mandrel cylinders 226, 228 and 230 respectively.

Follower mandrel 210 is disposed between plates 214 and 216, for rotation about a predetermined axis, with guide channels 244, 246 and 248, which corresponds in configuration to, and are in planar alignment with, guide channels 232, 234 and 236. Follower mandrel 210 is disposed inboard of primary mandrel 208 to facilitate rotation of capstan 206 through action of lever arm 212. The difference in diameters of the respective cylinders of follower mandrel 210 correspond to the difference in diameters of the cylinders of primary mandrel 208. The axis of rotation of follower mandrel 210 (defined by respective pins 250 which are received in corresponding bores in plates 214 and 216) is disposed relative to the axis of primary mandrel 208 such that channels 244, 246 and 248 are in relatively close proximity to channels 232, 234 and 236 of primary mandrel 208, so that the distance between the interior bottoms of the corresponding guide channels is a predetermined distance, preferably generally corresponding to the maximum cross-sectional rod diameter and guide channels 232 and 244, 234 and 246, and 236 and 248, cooperate to form respective bending channels.

Figure 5A:
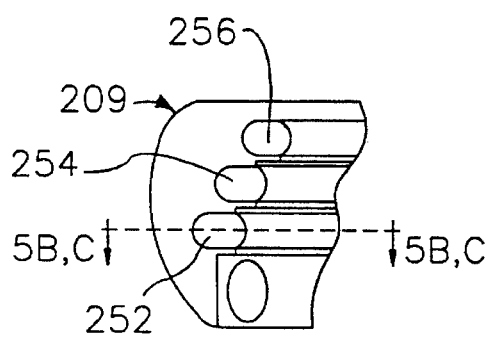
FIG. 5A is a side view of the gripping element of the apparatus of FIG. 2.
Figure 5B:
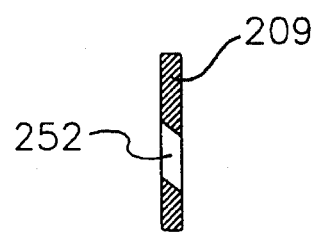
FIG. 5B is a sectional view of the gripping element of the FIG. 5A.
Figure 5C:
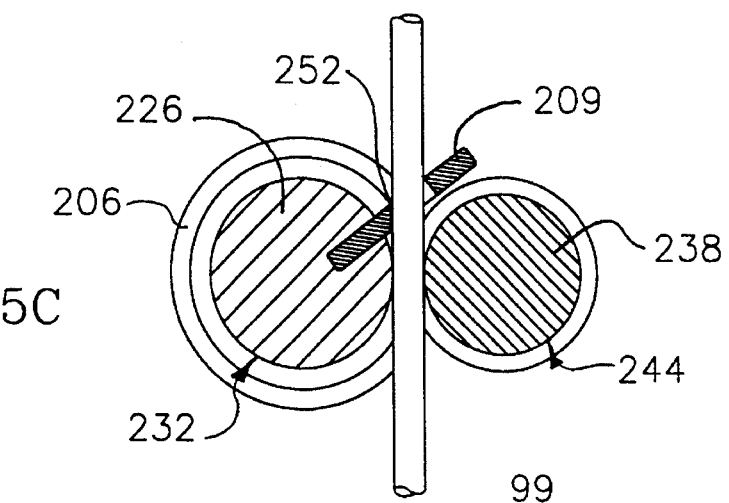
FIG. 5C is a sectional view illustrating the initial engagement of a rod by the apparatus of FIG. 2.
Figure 6A:
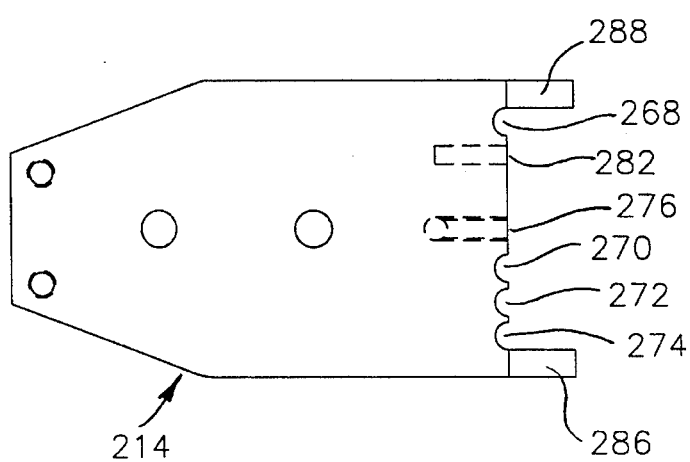
FIGS. 6A, 6B and 6C are top, elevation and side views of the base plate of the apparatus of FIG. 2.
Figure 6B:
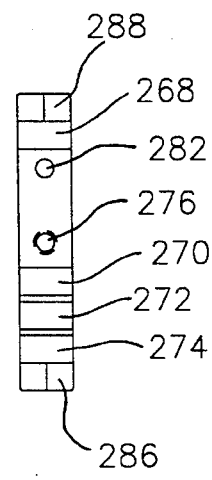
Figure 6C:
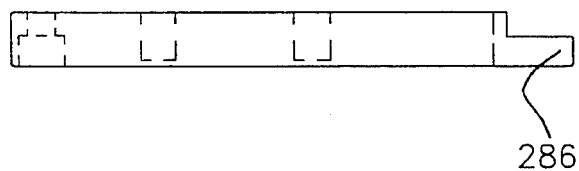
Figure 7:
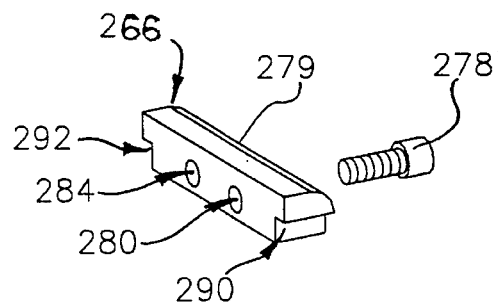
FIG. 7 is a perspective view of the fulcrum bar of the apparatus of FIG. 2.

Referring now to FIGS. 2, 5A and 5B, gripping member 209 is mounted for rotation with primary mandrel 208, effectively enclosing a portion of the guide channels 232, 234 and 236 of cylinders 226, 228 and 230, to form respective passageways 252, 254 and 256 (FIG. 5A). Passageways 252, 254 and 256 are suitably formed by boring holes through plate 209, at a predetermined angle with respect to the plate sides, i.e. with respect to a radius of mandrel 208. The angle and configuration of passageways 252, 254 and 256 are such that when primary mandrel 208 is rotated into a predetermined position, passageways 252, 254 and 256 are in alignment with the respective guide channels of the corresponding mandrel cylinders. As shown in FIG. 5C, rod 99 can be journaled through passageway 252, and through respective guide channels 232 and 244. In the preferred embodiment, passageways 252, 254 and 256 comprise bores of diameters slightly greater than the maximum rod diameter, disposed at an angle of approximately 53° relative to a radial line from primary mandrel 208.

In operation, primary mandrel is rotated to bring passageways 252, 254 and 256 into alignment with the respective bending channels formed between primary mandrel 208 and follower mandrel 210 (FIG. 5C). Rod 99 is then journaled through the passageway corresponding to the cylinder having the desired diameter of curvature, e.g. primary mandrel cylinder 232. The second lever arm 212 is engaged in one of the capstan holes 220. Lever arms 204 and 212 are then forced toward each other to rotate capstan 206, and hence primary mandrel 208 in, e.g. a counter-clockwise direction. As mandrel 208 is rotated, the passageway, e.g. 252, through which rod 99 is journaled, effectively engages rod 99, exerting angular force on rod 99. Passageway 252 forces rod 99, at the point of engagement, to be approximately tangent to the cylinder of primary mandrel 208. Follower mandrel 238 rolls against rod 99. Rod 99 thus follows the perimeter of primary mandrel cylinder 226, making rod 99 tend to rotate with primary mandrel 208. Follower mandrel 210, however, forces rod 99 to be tangent to mandrels 208 and 210 in the bending channel between the mandrels, causing rod 99 to bend into conformance with the periphery of guide channel 232.

Mandrels 208 and 210, and gripping plate 209, are all formed of an autoclavable material of a predetermined hardness material of a hardness significantly in excess of the maximum hardness of rod 99. Specifically, the rods from which implants are typically formed, are 316 LVM stainless steel, or titanium 6 aluminum, 4 vanadium and stainless steel. Preferably, the mandrels are harder by 20%, and preferably at least 30% or 40%, than the maximum rod hardness. For example in the preferred embodiment, mandrels 208 and 210 and gripping plate 209 are formed of 17-4 hardenable stainless steel hardened to approximately 40 to 45 Rockwell C. If the mandrels and gripping plate are not sufficiently harder than the rod, the mandrels are deformed during the bending operation, and ultimately no longer create uniform curvatures. In addition, if the mandrels are not sufficiently hard relative to the rods, or were not autoclavable without oxidation, foreign material, e.g. a layer or flakes of metal, or oxide, would tend to be transferred to the implant to the detriment of the patient. It has been determined that if the mandrels are formed of an autoclavable material of appropriate hardness, such a transfer will not occur.

If desired, a gauge 260 can be provided in top plate 216 to facilitate centering the U-shaped bridge to be formed at a particular point in the rod. A slot 262 is formed in top plate 216, preferably having an angled surface. Respective gauge lines 264 are formed corresponding to the respective cylinders of primary mandrel 208. The desired center point on the rod (typically, but not necessarily, the center of the rod, so that the implant legs are of equal length) is marked on the rod. When the rod is journaled through with a gripping passageway of gripping element 209 and the bending channel formed between mandrels 208 and 210, the mark aligned with the guide marking 264 corresponding to the particular cylinder through which the rod is journaled, the resultant bend will take place in the center of the rod.

Thus, a straight rod can be bent into a U shape. If desired, a mechanism can also be provided to effect bending of the U-shaped (arcuate) bridge of the implant to a predetermined transverse angle. Referring now to FIGS. 2, 6A, 65, 6C, 7, a radiused edge fulcrum plate (pinch plate) can be provided at the distal end of base plate 214. Specifically, a radiused edged fulcrum plate 266 is disposed for controlled axial movement relative to the end of base plate 214, to operate, in effect, as a vice to engage and tightly clamp the legs of the partially formed U-shaped implant rod, and act as a fulcrum against which the bridge portion of the implant can be bent. Respective notches 268, 270, 272, and 274 are formed in the distal edge of base plate 214. Notches 268, 270, 272 and 274 are configured to receive the legs of the U-shaped rod after it has been bent in the mandrel section, as can best be seen in FIGS. 2 and 6A. Notches 270, 272 and 274 are disposed at distances from notch 268 corresponding to the diameters of curvature of the respective cylinders of primary mandrel 208. A threaded axial bore 276 is provided to engage a threaded shaft of a tightening knob 278, which is journaled through a corresponding axial bore 280 in fulcrum plate 209. A guide pin (not shown) is journaled in an offset axial bore 282 in the distal end of base plate 214, and a corresponding axial bore 284, to maintain alignment. In addition, respective support shelves 286 and 288 (FIGS. 6A and 6C) are provided, extending axially from the distal edge of base plate 214. Corresponding notches 290 and 292 (FIG. 7) are formed in radiused fulcrum bar 209. The upper edge of fulcrum bar 209 manifests a predetermined radius corresponding to the desired angle to which the arcuate bridge is to be bent.

Lever arm 212 suitably includes a paddle shaped portion 294 at the end opposite to that which is received by capstan 206. A bridge 296 is provided on one side of paddle 294 in proximity to the panel end, forming a channel for receiving the U-shaped bridge of the partially formed implant. In operation, after the rod is bent into a U-shape using mandrels 208 and 210, the legs of the U are inserted downwardly into notch 268, and corresponding notch 270, 272, or 274. The legs are then tightly clamped by by fulcrum bar 209 by tightening knob 278. Notches 290 and 292 ride on shelves 286 and 288. The position of the legs adjacent to radiused edge 279 corresponds to the position at which the bend is desired. Such position is dictated by the anatomy of the patient, and is determined by the surgeon, with the aid of pre-operation x-rays and imaging, and visual inspection during the operation. Lever arm paddle 294 is disposed to engage the bridge of the U-shaped rod, with the rod received between the surface of paddle 294 and bridge 296. Lever arm 212 is then cantilevered away from mandrel housing 202 (in a counter-clockwise direction) to cause the legs of the U-shaped rod to bend to conformity with the radiused edge of fulcrum bar 209.

If desired, paddle 294 can also include gauge markings corresponding to the respective diameters of curvature provided by the respective cylinders of primary mandrel 208, for use by the surgeon in gauging the appropriate sizing.

It should be appreciated that surgical rod bender 200 is particularly advantageous in a number of respects. The device provides uniform and consistent implants in a matter of a few moments. Further, the process inflicts relatively few mars on the surface of the rod during the formation process.

The rotation of follower mandrel 210, and relatively large engaging surface of gripping rod passageway 252 tend to minimize scratches, nicks, and other marring. Thus, the potential of high stress in the bent rod, and potential failure of the rod either during the bending process or after the device has been implanted, is minimized. Moreover, the disposition of mandrels 208 and 210 within the interior of housing 202, effectively shrouds the area where bending is taking place. Thus, in the event of a fracture of the rod during bending, the combination of the box-like shape of the housing, and the action of grip plate 209 to hold onto metal fragments minimize the risk of injury due to flying metal fragments.

In addition, the device is readily disassemblable and easily sterilized. The device can be disassembled by removal of two bolts affixing the proximal end of base plate 214 to end plate 218. The axial pins of mandrels 208 and 210 are received in respective apertures in plates 214 and 216. Removal of base plate 214, frees mandrels 208 and 210 for removal. Alignment during the assembly presents no problem; the respective mandrel pins are simply reinserted in the respective apertures and base plate 214 reaffixed to end plate 218. In addition, sets of interchangeable mandrels having various diameters, and combination of diameters can be employed to provide a wide range of curvature diameters. Likewise, various interchangeable fulcrum bars 209 can be employed, each having a different radius to control the bend angle of the bridge. Further, the device avoids transfer of foreign particles to the implant and noted above. Further, there are no closed holes or features of the device that cannot be easily cleaned, so that blood and tissue debris will not be retained on the device.

It will be understood that the above description is of preferred exemplary embodiments of the present invention, and the invention is not limited to the specific form shown. Modifications may be made in the design and arrangement of the elements within the scope of the invention, as expressed in the claims.

I claim:

1. Apparatus for bending a metal rod with a predetermined maximum hardness characteristic to form a surgical implant in a sterile operating room environment, with minimal nicking and scratching of, and minimal transfer of foreign material to, the rod, the apparatus comprising:

a mandrel housing including first and second generally parallel housing plates having proximal and distal ends, and a transversely disposed end piece removably connecting the plates:

a first lever arm extending rearwardly from the mandrel housing in a plane generally parallel to the planes of the plates;

a capstan rotatably disposed between the plates, a second lever arm adapted to engage the capstan to facilitate rotation thereof;

the capstan comprising a cylinder of predetermined radius and height, including a plurality of radially disposed bores of a predetermined diameter, the capstan bores being adapted to receive a first end of the second lever arm and disposed in the same plane as the first lever arm, such that the first and second lever arms can be moved toward each other during the bending process without generating any spurious torques;

a primary mandrel axially aligned with the capstan and fixed thereto for rotation therewith, the primary mandrel having at least one generally cylindrical portion with a guide channel formed in the circumferential surface thereof, a follower mandrel, having at least one generally cylindrical portion with a guide channel formed in the circumferential surface thereof, the follower mandrel being rotatably disposed in the mandrel housing and axially offset from the first mandrel by a predetermined distance generally corresponding to the diameter of the rod, with the guide channel of the follower mandrel being in planar alignment with the guide channel of the primary mandrel to form a bending channel therebetween;

a gripping member mounted for rotation with the primary mandrel, the gripping member enclosing a portion of the guide channel of the primary mandrel cylindrical portion to thereby form an enclosed passageway of predetermined configuration;

the passageway being configured such that when the primary mandrel is rotated to a predetermined starting position, the passageway is brought into general alignment with the bending channel, and the rod can be journaled through the passageway and into the bending channel;

the housing, first lever arm, second lever arm, capstan, primary mandrel, gripping member and follower mandrel each being formed of an autoclavable material with a predetermined hardness at least equal to the maximum hardness of the rod;

rotation of the primary mandrel, with a rod journaled through the gripping member passageway and bending channel, causing the gripping member passageway to engage the rod, and pull the rod through the bending channel, to bend the rod into conformance with the primary mandrel cylindrical portion.

2. The apparatus of claim 1 wherein the capstan includes four radially disposed bores.

3. The apparatus of claim 1 wherein:

the primary mandrel comprises a predetermined number of stacked cylinders of decreasing diameter;

the follower mandrel comprises a predetermined number of corresponding stacked cylinders of increasing diameter; and each of the cylinders includes:

a respective peripheral guide channel, with the peripheral guide channels of corresponding cylinders in planar alignment to form respective bending channels therebetween; and a respective gripping member, mounted for rotation with the primary mandrel, which encloses a portion of the guide channels of the primary mandrel cylinders, to form respective passageways of predetermined configuration.

4. The apparatus of claim 3 wherein the difference in diameters of the respective adjacent cylinders of the follower mandrel correspond to the difference in diameters of the adjacent cylinders of the primary mandrel.

5. The apparatus of claim 3 wherein the primary mandrel comprises three stacked cylinders.

6. The apparatus of claim 5 wherein the diameters of the primary mandrel cylinders are 1¼ inch, 1 inch, and ¾ of an inch.

7. The apparatus of claim 3 wherein the gripping member comprises a plate with through holes disposed at a predetermined angle with respect to a radius of the primary mandrel, such that when the primary mandrel is in a predetermined position, the gripping member passageways are in alignment with the respective bending channels.

8. The apparatus of claim 7 wherein the gripping member passageways comprise bores of diameters slightly greater than the maximum rod diameter to be bent, disposed at an angle of approximately 53° relative to a radial line from the primary mandrel.

9. The apparatus of claim 1 wherein the gripping member comprises a plate with a through hole disposed at a predetermined angle with respect to a radius of the primary mandrel, such that when the primary mandrel is in a predetermined position, the gripping member passageways are in alignment with the bending channels.

10. The apparatus of claim 9 wherein the gripping member passageway comprises a bore of a diameter slightly greater than the maximum rod diameter to be bent, disposed at an angle of approximately 53° relative to a radial line from the primary mandrel.

11. The apparatus of claim 1 wherein the follower mandrel is disposed inboard of the primary mandrel to facilitate rotation of the capstan through action of the second lever arm.

12. The apparatus of claim 1 wherein the mandrels are harder, by at least 20%, than the maximum hardness of the rods to be bent.

13. The apparatus of claim 1 wherein the mandrels are harder, by at least 30%, than the maximum hardness of the rods to be bent.

14. The apparatus of claim 1 wherein the mandrels are harder, by at least 40%, than the maximum hardness of the rods to be bent.

15. The apparatus of claim 2 wherein the mandrels and gripping member are formed of 17-4 hardenable stainless steel hardened to approximately 40 to 45 Rockwell C.

16. The apparatus of claim 1 further including a gauge provided in the first housing plate to facilitate centering a U-shaped bridge to be formed at a particular point in the rod.

17. The apparatus of claim 16 wherein the gauge comprises a slot formed in the first plate and respective gauge lines corresponding to each cylinder of the primary mandrel.

18. The apparatus of claim 1 further including a radiused edge fulcrum plate disposed for controlled axial movement relative to the distal end of the housing second plate, for engaging rods placed between the fulcrum plate and the end of the housing second plate, and acting as a fulcrum against which the rod can be bent.

19. The apparatus of claim 18 wherein the second lever arm includes:

a paddle shaped portion at a second end opposite to the first end which is received by the capstan; and a bridge is provided on one side of the paddle portion in proximity to a distal end thereof, forming a channel for receiving a rod.

* * * * *